US012758434B2

(12) United States Patent
Bäck et al.

(10) Patent No.: US 12,758,434 B2
(45) Date of Patent: Oct. 13, 2026

(54) METHOD OF PRODUCING PANT-TYPE ARTICLES

(71) Applicant: Essity Hygiene and Health Aktiebolag, Gothenburg (SE)

(72) Inventors: Lucas Bäck, Gothenburg (SE); Fanny Stenholm, Gothenburg (SE); Helena Wallin, Gothenburg (SE); Johannes Lanooij, Ah Zeist (NL)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 156 days.

(21) Appl. No.: 18/567,855

(22) PCT Filed: Jun. 9, 2021

(86) PCT No.: PCT/EP2021/065375

§ 371 (c)(1),
(2) Date: Dec. 7, 2023

(87) PCT Pub. No.: WO2022/258159

PCT Pub. Date: Dec. 15, 2022

(65) Prior Publication Data

US 2024/0277529 A1 Aug. 22, 2024

(51) Int. Cl.
*A61F 13/15* (2006.01)

(52) U.S. Cl.
CPC .. *A61F 13/15585* (2013.01); *A61F 13/15699* (2013.01); *A61F 13/15723* (2013.01)

(58) Field of Classification Search
CPC .......... A61F 13/15585; A61F 13/15699; A61F 13/15723; A61F 2013/49082;
(Continued)

(56) References Cited

U.S. PATENT DOCUMENTS

| | | | |
|---|---|---|---|
| 6,358,350 B1 | 3/2002 | Glaug et al. | |
| 2004/0040642 A1 | 3/2004 | Otsubo et al. | |

(Continued)

FOREIGN PATENT DOCUMENTS

| | | |
|---|---|---|
| CO | 5590881 A2 | 12/2005 |
| EP | 3095423 A1 | 11/2016 |

(Continued)

OTHER PUBLICATIONS

International Search Report (PCT/ISA/210) and Written Opinion (PCT/ISA/237) mailed on Apr. 7, 2022, by the European Patent Office as the International Searching Authority for International Application No. PCT/EP2021/065375.

(Continued)

*Primary Examiner* — George R Koch
*Assistant Examiner* — Christopher C Caillouet
(74) *Attorney, Agent, or Firm* — Buchanan Ingersoll & Rooney PC

(57) ABSTRACT

A method for continuously producing disposable pant-type articles from webs moving in a machine direction, the method including attaching a non-elastic crotch web between a tensioned elastic front panel web and a tensioned elastic rear panel web to form a coherent chassis web of interconnected precursor articles and attaching a pair of stretched crotch elastic members to the chassis web in each precursor article with the crotch elastic members being arranged in a cross machine direction, whereafter leg cuts are formed in the chassis web between the precursor articles, the chassis web is folded along a fold-line extending in the machine direction, first and second side seams are formed in each precursor article, along dividing lines between the precursor articles, the side seams being formed from the aligned waist edges of the precursor articles, to the leg cuts,
(Continued)

and finally severing individual pant-type articles from the chassis web.

17 Claims, 9 Drawing Sheets

(58) Field of Classification Search
CPC ............ A61F 13/15804; A61F 13/4906; A61F 13/496; A61F 13/15593
See application file for complete search history.

(56) References Cited

U.S. PATENT DOCUMENTS

| | | | |
|---|---|---|---|
| 2009/0320993 A1 | 12/2009 | Yamamoto | |
| 2009/0326503 A1 | 12/2009 | Lakso et al. | |
| 2011/0209270 A1* | 9/2011 | Carlson | A61F 13/15593 2/400 |
| 2018/0256410 A1 | 9/2018 | Bäck et al. | |
| 2018/0333943 A1* | 11/2018 | Middlesworth | B65H 23/1888 |

FOREIGN PATENT DOCUMENTS

| | | | |
|---|---|---|---|
| EP | 3117810 | A1 | 1/2017 |
| EP | 3326596 | A1 | 5/2018 |
| JP | 2000126230 | A | 5/2000 |
| JP | 2003339768 | A | 12/2003 |
| JP | 2009536845 | A | 10/2009 |
| JP | 2010142499 | A | 7/2010 |
| JP | 2014004258 | A | 1/2014 |
| JP | 2020520705 | A | 7/2020 |
| WO | 2004078083 | A1 | 9/2004 |
| WO | 2007133127 | A1 | 11/2007 |
| WO | 2011162652 | A1 | 12/2011 |
| WO | 2012053945 | A1 | 4/2012 |
| WO | 2014002440 | A1 | 1/2014 |
| WO | 2017044013 | A1 | 3/2017 |
| WO | 2017044014 | A1 | 3/2017 |
| WO | 2020032841 | A1 | 2/2020 |

OTHER PUBLICATIONS

Office Action (Notice of Reasons for Rejection) issued on Oct. 7, 2024, by the Japanese Patent Office in corresponding Japanese Patent Application No. 2023-575928, and an English Translation of the Office Action. (12 pages).

Office Action issued on Jan. 28, 2025, by the Japanese Patent Office in corresponding Japanese Patent Application No. 2023-575928, and an English Translation of the Office Action. (7 pages).

Office Action issued on Dec. 5, 2025, by the Brazilian Patent Office in corresponding Brazilian Patent Application No. BR112023024752-7, English translation only. (8 pages).

Office Action issued on Jan. 5, 2026, by the Colombian Patent Office in corresponding Colombian Patent Application No. NC2023/0017004, and a partial English Translation of the Office Action. (11 pages).

* cited by examiner

METHOD OF PRODUCING PANT-TYPE ARTICLES

TECHNICAL FIELD

The present disclosure pertains to a method of producing disposable pant-type articles, the method comprising advancing a continuous elastic front panel web, a continuous elastic rear panel web and a non-elastic continuous crotch web in a machine direction and attaching the crotch web along crotch edges of the front panel web and the rear panel web to form a continuous composite chassis in which leg cuts are formed whereafter the chassis web is folded along a fold-line extending in the machine direction, side seams are formed to delimit precursor articles in the chassis web from each other and individual pant-type articles are severed from the continuous chassis web. The disclosure further pertains to a disposable pant-type article being produced by the method.

BACKGROUND

In the art of disposable pant-type articles and in particular disposable pant-type articles which are intended for use by adult users, the articles should meet high demands on fit, comfort and have a tailored and underwear like appearance while at the same time meeting equally high demands on absorbency and leakage protection. Disposable absorbent articles are articles which are intended to be discarded after a single use and not be laundered or otherwise restored for repeated use.

Pant-type articles of this kind are relatively complex products involving multiple components which are combined to form the final absorbent article. Such components include nonwoven components, barrier components, elastic components and usually an absorbent core which may be provided in the form of an absorbent assembly including a barrier layer and a liquid permeable topsheet which together enclose the absorbent core. The production of pant-type articles involves handling components having different physical form such as planar webs, elongated elastic elements, loose fibres, particles or components being in fluid form such as adhesives, as well as components differing in physical properties such as stretchability, stiffness, thickness porosity, etc. Some components may require raised application temperature e.g., thermoplastic binders.

The manufacture of pant-type articles involves complicated and complex processes requiring process equipment and procedures which enable all the different components to be processed and combined to produce the final article and there is an on-going need for a cost-efficient method of producing high-quality disposable pant-type articles.

The present disclosure aims at offering an improved, economically viable and efficient method for producing pant-type articles comprising multiple components.

SUMMARY

According to the method of claim 1, disposable pant-type articles having good functionality both with regard to leakage security and with regard to appearance, fit, and comfort may be produced. Variations of the disclosure are set out in the dependent claims.

Disclosed herein is a method of producing disposable pant-type articles, the method comprising the steps of:

- advancing a continuous elastic front panel web in a machine direction, the front panel web being tensioned in the machine direction and having a front panel waist edge and an opposing front panel crotch edge;
- advancing a continuous elastic rear panel web in a machine direction, the rear panel web being tensioned in the machine direction and having a rear panel waist edge and an opposing rear panel crotch edge, the rear panel web being spaced apart from the front panel web in a cross machine direction, perpendicular to the machine direction, with a gap in the cross machine direction between the front panel crotch edge and the rear panel crotch edge;
- advancing a non-elastic continuous crotch web in the machine direction;
- attaching the crotch panel web to the tensioned front panel web and to the tensioned rear panel web, thereby bridging the gap between the front panel web and the rear panel web and forming a coherent chassis web of interconnected precursor articles;
- providing a pair of crotch elastic members, the pair of crotch elastic members consisting of a first crotch elastic member and a second crotch elastic member;
- stretching each crotch elastic member in a longitudinal direction of the crotch elastic member and aligning the longitudinal direction of the crotch elastic member with the cross machine direction;
- attaching each stretched crotch elastic member to the crotch web while keeping the crotch elastic member stretched and aligned with the cross machine direction, the first crotch elastic member being spaced apart from the second crotch elastic member with a crotch spacing in the machine direction, a pair of crotch elastic members of a trailing precursor article being spaced apart from a pair of crotch elastic members of a leading precursor article with an article spacing in the machine direction, the article spacing corresponding to a pitch-length of the precursor articles in the chassis web of interconnected precursor articles;
- forming leg cuts in the chassis web between the precursor pant type articles, each leg cut having a closed loop configuration and forming a first leg edge of a leading precursor article and a second leg edge of a trailing precursor article;
- folding the chassis web along a fold-line extending in the machine direction and bringing the waist edge of the front panel web into alignment with the waist edge of the rear panel web;
- forming first and second side seams in each precursor article, the side seams being formed in the cross machine direction along dividing lines between the precursor articles, from the aligned waist edges of the front and rear panel webs, to the leg cuts; and
- severing individual pant-type articles from the chassis web.

The non-elastic, non-stretchable continuous crotch web may be a crotch panel web having a first side edge and an opposing second side edge. Attaching the crotch web to the tensioned front panel web and to the tensioned rear panel web may comprise;

- attaching the first side edge of the crotch web to the tensioned front panel web along the front panel crotch edge, such as in an overlap seam extending along the front panel crotch edge; and attaching the second side edge of the crotch web to the tensioned rear panel web along the rear panel crotch edge; such as in an overlap seam extending along the rear panel crotch edge.

Alternatively, the non-elastic, non-stretchable continuous crotch web may be an outer or inner cover web extending in the cross machine direction the full distance or at least 75% of the distance between the front waist edge and the rear waist edge.

The elastically stretchable front panel web and/or the elastically stretchable rear panel web may comprise or consists of an elastic laminate, the elastic laminate comprising at least a first layer of fibrous material and an elastic layer.

The elastic laminate may comprise a second layer of fibrous material and the elastic layer may be an intermediate elastic layer arranged between a first and a second layer of fibrous material.

The elastic layer in a laminate as disclosed herein may comprise or consists of a layer of elastic film.

The elastic layer in a laminate as disclosed herein may comprise or consists of a layer of elastic nonwoven material.

The front and rear panel webs may be the same or different types of webs.

One or both of the front panel web and the rear panel web may comprise or consists of a tri-laminate web comprising two outer nonwoven layers and an intermediate elastic layer between the outer nonwoven layers. A three-layer laminate in the front and/or rear panels may also be formed by a two-layer front web laminate and/or a two-layer rear web laminate together with an outer or inner crotch web which is bonded to the elastic front and/or rear panel webs.

A three-layer nonwoven-film-nonwoven laminate provides elastic panels with smooth, soft and skin-friendly textile-like surfaces. The laminate may be produced by any known method or combination of methods such as stretch-bonding methods, methods involving incremental stretching, etc.

A three-layer elastic panel web may be formed by stretch-bonding a first surface of an elastic layer, such as an elastic film, an elastic nonwoven or by stretch-bonding multiple parallel elastic elements such as strings or filaments to a first nonwoven layer and subsequently bonding a second nonwoven layer to a second surface of the elastic layer or to cover the multiple parallel elastic strings on the first nonwoven layer. Stretch bonding implies that the elastic layer or the elastic elements are stretched, such as by 50-600% in the machine direction MD, to retain the elastic properties of the elastic film layer in the compound base web. Bonding may be performed by any suitable technique such as ultrasonic bonding, adhesive bonding, heat bonding, etc.

When using laminate elastic panel webs comprising a stretch-bonded elastic layer or elastic elements and one or more non-elastic layers, non-stretchable layers, such as one or more non-stretchable nonwoven layers in the method as disclosed herein, the webs are held tensioned, throughout the process up until the final step of severing individual pant-type articles from the chassis web. This generally means that the webs are stretched in the machine direction to the maximum extent permitted by the non-stretchable layer or layers.

The crotch web as disclosed herein may be any suitable non-elastic, non-stretchable web material, such as a non-stretchable nonwoven web, a non-stretchable polymer film. Laminates comprising one or more nonwoven webs and laminates comprising one or more nonwoven webs and a polymer film are also conceivable.

In the method as disclosed herein, the crotch elastic members may be band-shaped crotch elastic members. The band-shaped crotch elastic members may be strips of inherently elastic material such as elastic film or elastic nonwoven material or may be pre-fabricated elastic members comprising one or more layers of non-elastic webs to which one or more elastic elements have been bonded in a tensioned state. Such elastic elements may be multiple elastic strings, threads or bands which are applied parallel to each other in the length direction of the crotch elastic member corresponding to the cross machine direction of the method and which are spaced-apart in the width direction of the crotch elastic member, corresponding to the machine direction of the method. Laminates of elastic film and one or more non-elastic nonwoven webs are also contemplated for the crotch elastic members as disclosed herein.

In the method as disclosed herein, it may be preferred that the crotch elastic members comprise or consist of elastic film.

The stretched crotch elastic members may have a width as measured in the machine direction in the range of from 15 mm to 50 mm, such as from 20 mm to 40 mm or from 25 mm to 35 mm, and a length as measured in the cross machine direction in the range of from 150 mm to 350 mm, such as from 170 mm to 320 mm or from 200 mm to 310 mm.

The method as disclosed herein may further comprise applying and attaching an absorbent assembly comprising an absorbent core between the first and second leg edges of each precursor article in the chassis web, the absorbent core of the absorbent assembly being enclosed between a liquid impermeable backsheet and a liquid permeable topsheet. The absorbent assembly has side edges extending in a longitudinal direction of the absorbent assembly corresponding to the cross machine direction of the method and end edges extending in a cross direction of the absorbent assembly, corresponding to the machine direction of the method. The absorbent assembly may further comprise additional elastic elements such as raised elastic barriers or shaping elastic.

The absorbent assembly may be applied to cover the stretched and attached crotch elastic members. In this manner the absorbent assembly will be overlaying the crotch elastic members on the inner surface of the final pant-type article, the inner surface being the surface which is intended to be facing the wearer when the pant-type article is being worn. The inner surface of the absorbent assembly may be formed by the liquid permeable topsheet and may optionally include barrier cuffs extending along the side edges of the absorbent assembly.

It may be preferred that the topsheet of the absorbent assembly and any barrier cuffs are formed from fibrous web material, such as nonwoven material, providing the inner surface of the absorbent assembly with a textile character.

A part of each leg cut which extends in the crotch web may be cut through the crotch web, through the corresponding crotch elastic member and through a peripheral edge portion of the absorbent assembly, the peripheral edge portion of the absorbent assembly being formed by one or both of the liquid impermeable backsheet and the liquid permeable topsheet of the absorbent assembly, the peripheral edge portion of the absorbent assembly being arranged outward of a peripheral edge of the absorbent core of the absorbent assembly. In an absorbent assembly as disclosed herein, the topsheet and the backsheet may both extend beyond the periphery of the absorbent core and may be joined to each other in an edge seal extending along the periphery of the absorbent core outward of a peripheral edge of the absorbent core. The final pant-type absorbent article which is produced in this way will have smooth non-wrinkled elastic leg edges which conform comfortably to the groin of a wearer.

The method as disclosed herein may further comprise stretching a continuous reinforcing leg elastic member in the machine direction and attaching the continuous reinforcing leg elastic member in a stretched state in a curved configuration along the crotch edge of the tensioned rear panel web before forming the leg cuts in the chassis web. The continuous leg elastic member may comprise multiple individual elastic elements, such as 2 to 15 elastic elements, 3 to 12 elastic element or 4 to 10 elastic elements.

The multiple individual elastic elements may be elastic strings, threads or bands which are applied spaced apart in the machine direction.

The continuous leg elastic member may be applied with different tensioning along the continuous leg elastic member, such as with lower tensioning in the part of the leg elastic member extending between the first and the second leg openings than in the parts of the leg elastic member which are arranged to be extending along the leg edges. The lower tensioning may be attained by different stretching of the different parts of the leg elastic member and/or by neutralizing the elasticity of the leg elastic member in selected portions thereof.

Attaching the continuous reinforcing elastic element may comprise forming an attachment area or multiple attachment areas on the tensioned rear panel web by applying adhesive to the tensioned rear panel web; attaching the continuous reinforcing elastic element to the tensioned rear panel web in the attachment area or attachment areas; and optionally covering the reinforcing elastic element and the attachment area or attachment areas with a nonwoven covering web.

The method as disclosed herein may comprise overlapping a first end portion of each of the first and the second crotch elastic members of the pair of crotch elastic members with the tensioned front panel web and attaching the overlapping first end portion of each of the first and the second crotch elastic member to the tensioned front panel web and/or overlapping a second end portion of each of the first and the second crotch elastic members of the pair of crotch elastic members with the tensioned rear panel web and attaching the overlapping second end portion of each of the first and the second crotch elastic member to the tensioned rear panel web.

Alternatively, or in addition thereto, the second end portion of each of the first and the second crotch elastic members overlaps with and is attached to the tensioned rear panel web, and further overlaps with and is attached to the reinforcing elastic element.

When stretching and applying the stretched crotch elastic members to the chassis web, the end portions of the crotch elastic members may be held in movable clamps in a stretching device. The clamped end portions are not subjected to stretching and will be applied and attached to the chassis web in a non-tensioned condition. The two non-tensioned end portions of each crotch elastic member may have a combined extension in the cross machine direction (i.e. in the length direction of the crotch elastic members) of from 10% to 15% of the total extension of the stretched crotch elastic member in the cross machine direction.

The first and second crotch elastic members may be attached to the chassis web before or after attaching the reinforcing elastic element. In the embodiments where the second end portions of the first crotch elastic member and the second crotch elastic member overlaps with and are attached to the tensioned rear panel web, and further overlaps with and are attached to the reinforcing elastic element, it may be preferred that the reinforcing elastic element is attached to the second end portion of the first crotch elastic member and the second end portion of the second crotch elastic member.

It may be advantageous that the reinforcing elastic element is attached to non-tensioned end portions of the crotch elastic members as a more secure attachment between the reinforcing elastic element and the crotch elastic members may be obtained in this manner.

In the method as disclosed herein, the first leg edge of each precursor article in the chassis web may consists of:

- a front leg edge section extending in the tensioned front panel web;
- a crotch leg edge section extending in the crotch web between the front panel crotch edge and the rear panel crotch edge; and
- a rear leg edge section extending in the tensioned rear panel web; and the second leg edge of each precursor article consists of:

- a front leg edge section extending in the tensioned front panel web;
- a crotch leg edge section extending in the crotch web between the front panel crotch edge and the rear panel crotch edge; and
- a rear leg edge section extending in the tensioned rear panel web.

After application of a reinforcing elastic element on the tensioned rear panel web, the method as disclosed herein may further comprise forming the rear leg edge section of the first and second leg edges and simultaneously cutting away surplus parts of the reinforcing elastic element, leaving a remaining part of the reinforcing elastic element being attached along the rear leg edge section of each of the first leg edge and the second leg edge between a rearward point of each leg edge where the leg edge intersects with the rear panel crotch edge and a cutting point on the leg edge where the reinforcing elastic element is cut off. The reinforcing leg elastic member is preferably not attached to the chassis web between the leg edges and may be rendered inactive between the leg edges by being severed and allowed to snap-back to attachment areas arranged at the intersections between the rear leg edge sections and the crotch leg edge sections. In this way elastic contraction of the crotch area of the article and of an absorbent core which is present between the leg edges of the article may be avoided.

Thus, a portion of each rear leg edge section between the cutting point and the dividing line between adjacent precursor articles which is closest to the cutting point, may be free from reinforcing elastic. The portion of each rear leg edge section which is free from the reinforcing elastic element may have a length as measured along the corresponding leg edge from the cutting point to the closest dividing line which is from 25% to 75% of the total length of the rear leg edge section.

The method as disclosed herein may further comprise attaching a waist elastic member along the waist edge of the front panel web and/or along the waist edge of the rear panel web. The waist elastic member or waist elastic members may be attached to the waist edge of one or both of the front panel web and the rear panel web before being attached to the crotch web. The waist elastic member may be attached to the front panel web and the rear panel web in accordance with a method as disclosed in WO 2017/044013 A1 or WO 2017/044014 A1 involving attaching a continuous waistband component to a base web in a defined waistband attachment area and severing the base web and the attached waistband component along a cutting line extending through the attachment area in the machine direction thereby creating a first panel web comprising a first panel portion with a first portion of the waistband component attached thereto and a second panel web comprising a second panel portion and a second portion of the waistband component attached thereto. After severing the base web and the elastic waistband component, the two web parts are shifted in the cross machine direction such that the edges of the web parts along which the parts of the waistband component are attached are facing away from each other instead of facing towards each other. The two web parts with the attached parts of the waistband component may be used in the method of producing disposable pant-type articles as disclosed herein as a front panel web having a waist elastic member arranged along the waist edge of the front panel web and a rear panel web having a waist elastic member arranged along the waist edge of the rear panel web.

Alternatively, the waist elastic member may be attached to the waist edge of one or both of the front panel web and the rear panel web after attaching the front panel web and the rear panel web to the crotch web.

The waistband member is a component of the chassis web which is configured for creating a well-defined waistband in a final pant-type article as disclosed herein. Each waistband member has an outer edge facing away from the crotch edge of the corresponding panel web and an inner edge facing towards the crotch edge of the corresponding panel web. The inner edge of the waistband member constitutes a well-defined boundary between the waistband member and a body-portion of the corresponding panel web.

Depending on how the waistband member is applied to the a panel web, the waistband member may be completely overlapping with a waist edge part of the panel web, as in the application method disclosed in WO 2017/044013 A1 and WO 2017/044014 A1 or the waistband member may be attached to the waist edge of the panel web with only a small overlap, sufficient to create a join between the waistband member and the panel web.

The disclosure further pertains to a disposable pant-type article being produced by the method as disclosed herein, the method involving continuously producing disposable pant-type articles from webs moving in a machine direction. The method comprises attaching a non-elastic, non-stretchable crotch web between a tensioned elastic front panel web and a tensioned elastic rear panel web to form a coherent chassis web of interconnected precursor articles whereafter a pair of stretched crotch elastic members are attached to the chassis web in each precursor article with the stretched crotch elastic members being arranged in a cross machine direction. Leg cuts are then formed in the chassis web between the precursor articles. Subsequently, the chassis web is folded along a fold-line extending in the machine direction to bring the waist edges of the precursor articles into alignment with each other. First and second side seams are formed in each precursor article along dividing lines between the precursor articles, the side seams being formed from the aligned waist edges of the precursor articles to the leg cuts. Finally, individual pant-type articles are severed from the chassis web.

BRIEF DESCRIPTION OF THE DRAWINGS

The pant-type articles as disclosed herein will be further explained hereinafter with reference to the appended drawings wherein.

DETAILED DESCRIPTION

The method for producing a pant-type article as disclosed herein will be described more fully hereinafter with reference to the enclosed drawings. The drawings are schematic, and different parts and components are not necessarily drawn to scale.

The method is described herein in the context of a disposable pant-type article comprising an absorbent assembly. However, it is to be understood that the method is equally applicable to the production of absorbent and non-absorbent pant-type articles which do not comprise an absorbent assembly. The method as disclosed herein is useful in the production of any type of disposable pant-type article, such as adult incontinence articles, baby diapers, training pants, swim-pants, disposable underpants, sanitary pants for feminine use, etc.

A continuous method of producing disposable pant-type articles as disclosed herein will be described with reference to FIGS. 1-7.

Figure 1:
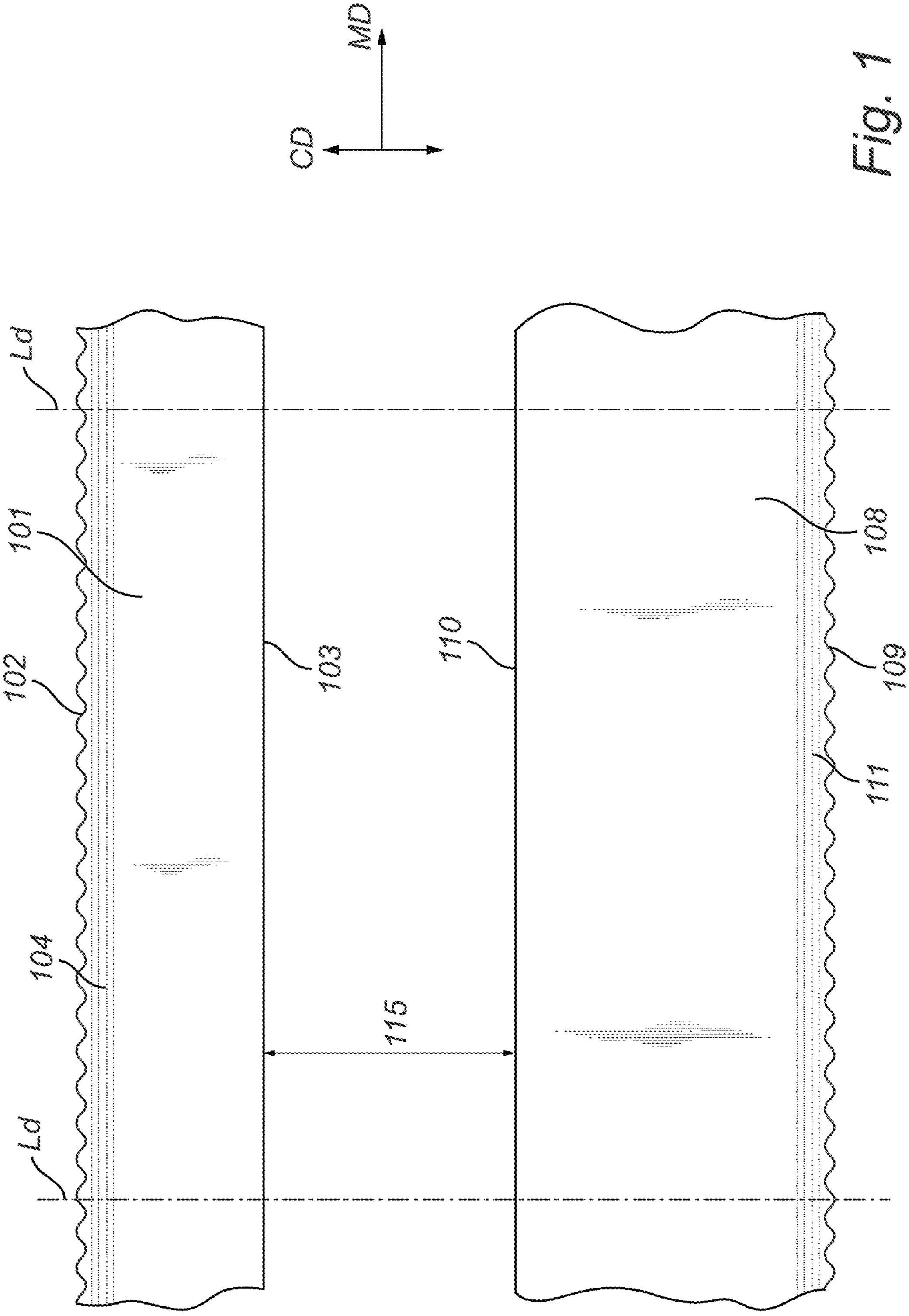
FIGS. 1-7 show a planar view of a section of a chassis web in progressing stages of production.

FIG. 1 shows a continuous elastic front panel web 101 which is being advanced in a machine direction MD. The front panel web 101 is advanced in the machine direction MD while being stretched in the machine direction MD such that the front panel web 101 is tensioned in the machine direction MD.

The front panel web 101 has a front waist edge 102 and an opposing front crotch edge 103.

FIG. 1 further shows a continuous elastic rear panel web 108 which is being advanced in the machine direction MD parallel to the elastic front panel web 101. The rear panel web 108 is advanced in the machine direction MD while being stretched in the machine direction MD such that the rear panel web 108 is tensioned in the machine direction MD.

The rear panel web 108 has a rear waist edge 109 and an opposing rear crotch edge 110. The rear panel web 108 is spaced apart from the front panel web 101 in a cross machine direction CD, perpendicular to the machine direction MD, with a gap 115 in the cross machine direction CD between the crotch edge 103 of the front panel web 101 and the crotch edge 110 of the rear panel web 108.

A front waist elastic member 104 is arranged along the front waist edge 102 and a rear waist elastic member 111 is arranged along the rear waist edge 109. The waist elastic members 104, 111 have been attached to the front panel web 101 and the rear panel web 108 prior to the production step shown in FIG. 1 e.g., by a method as disclosed in WO 2017/044013 A1 and WO 2017/044014 A1. The method in WO 2017/044013 A1 and WO 2017/044014 A1 starts from a base web to which a continuous waistband component is attached, whereafter the base web is cut in two parts along a cutting line extending in the machine direction and severing both the base web and the waistband component along the cutting line. By dividing the base web in two parts there is formed a first panel web having a first portion of the waistband component attached thereto and a second panel web having a second portion of the waistband component attached thereto. The two web parts are subsequently shifted in the cross machine direction such that the cut edges of the web parts along which the parts of the waistband component are attached are arranged facing away from each other. When the web parts are further processed in the method as disclosed herein, the cut edge of the first panel web forms the front waist edge 102 of the front panel web 101 and the cut edge of the second panel web forms the rear waist edge 109 of the rear panel web 108 as shown in FIG. 1. The divided waistband component forms the front waist elastic member 104 and the rear waist elastic member 111 on the respective front panel web 101 and rear panel web 108.

The method in WO 2017/044013 A1 and WO 2017/044014 A1 results in a front waist elastic member 104 which is coterminous with the front waist edge 102 of the front panel web 101 and a rear waist elastic member 111 which is coterminous with the rear waist edge 109 of the rear panel web 108. In the example shown in FIGS. 1-7, the front waist edge 102 and the rear waist edge 109 have matching sinusoidal configurations. It is to be understood that the waist edges need not have the undulating configuration shown in the Figures and that any other configuration may be used such as a straight edge, a zig-zag edge, etc. Furthermore, it is to be understood that other methods for attaching a waistband member to the front and rear panel webs may be used. The front waistband member may alternatively be attached with an edge seam along the front waist edge of the front panel web and the rear waistband member may be attached with an edge seam along the rear waist edge of the rear panel web. In such embodiments, the waistband members extend in the cross machine direction CD outward of the waist edge of the corresponding panel web. Another conceivable arrangement of the waistband members is to attach them slightly inward of the waist edges of the panel webs. In such embodiments, each waistband member is fully overlapping with the corresponding panel web, with a small edge portion of the panel web extending in the cross machine direction CD a distance in the order of 2 to 15 mm outward of the waist edge of the panel web.

Waistband members which are attached to the front panel web and the rear panel web by other methods than the method disclosed in WO 2017/044013 A1 and WO 2017/044014 A1, may be attached during any suitable stage of the method as disclosed herein or may be attached prior to the stage shown in FIG. 1. It is also to be understood that the waist elastic members as disclosed herein are optional to the method and the disposable pant-type articles as disclosed herein.

The waist elastic members may comprise or consist of any suitable elastic material or elasticated material as known in the art including elastic threads, elastic film, elastic nonwoven and elastic foam. Furthermore, an elastic member may be applied in the form of multiple elongated elastic elements, as a single band of elastic or elasticated material e.g., an elastic laminate. In all instances, the elastic member is a component of a chassis web or a disposable pant-type article as disclosed herein, which is separate and distinct from other elastification of the chassis web of the pant-type article such as leg elastic or body elastic.

Figure 2:
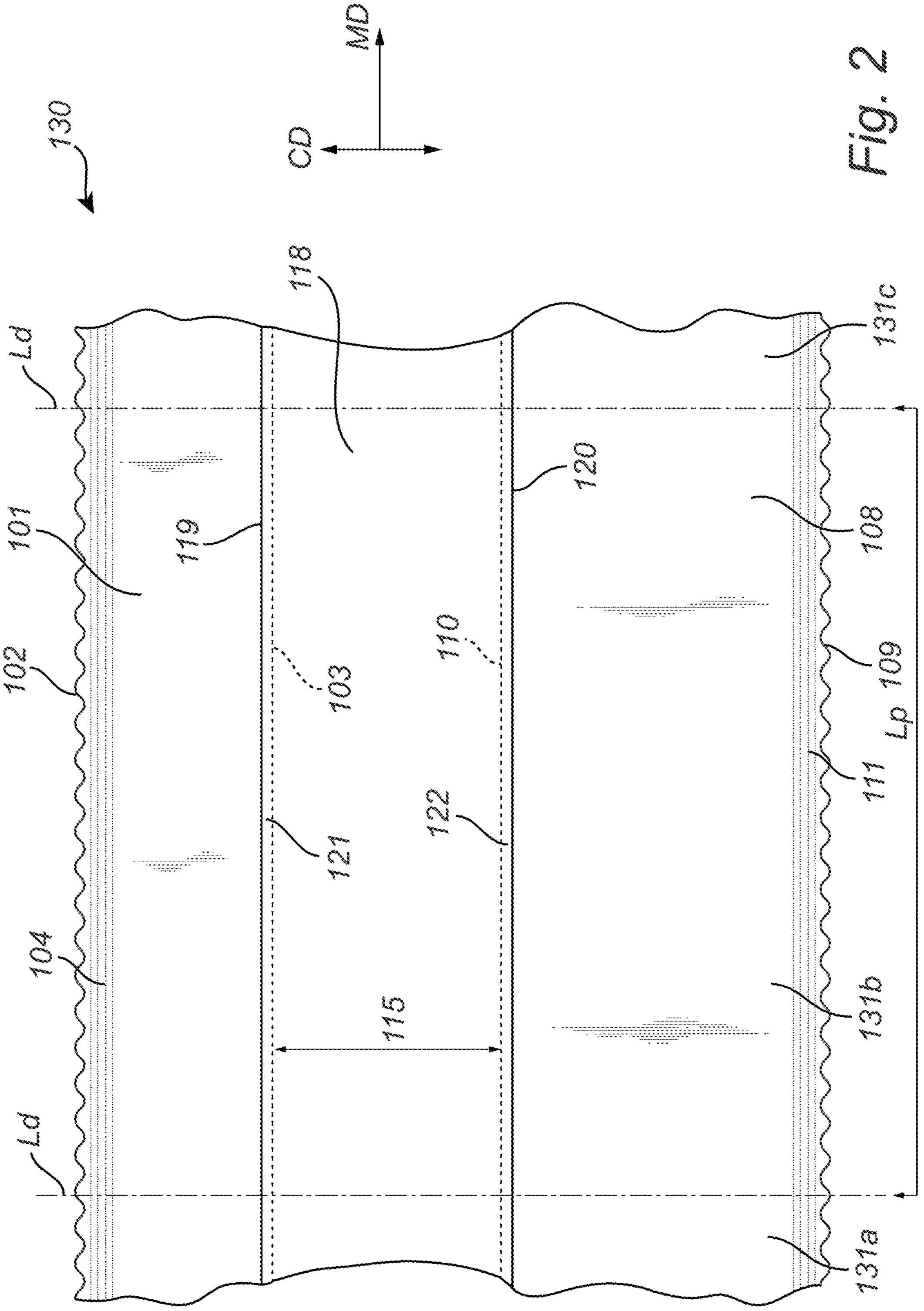

A non-elastic, non-stretchable continuous crotch web 118 having a first side edge 119 and an opposing second side edge 120 is then advanced in the machine direction MD and the first side edge 119 of the crotch web 118 is attached in a first overlap seam 121 along the crotch edge 103 of the tensioned front panel web 101 and the second side edge 120 of the crotch web 118 is attached in a second overlap seam 122 along the crotch edge 110 of the tensioned rear panel web 108, as shown in FIG. 2. The crotch web 118 bridges the gap 115 between the front panel web 101 and the rear panel web 108 to form a coherent chassis web 130 of interconnected precursor articles 131*a*, 131*b*, 131*c*, being delimited by dividing lines Ld extending in the cross machine direction CD, each precursor article 131*a*, 131*b*, 131*c* having a pitch-length Lp in the machine direction MD between the dividing lines Ld. The pitch-length Lp of the precursor articles 131*a*, 131*b*, 131*c* remains the same until the final step of the method as disclosed herein, when individual pant-type articles are severed from the chassis web 130.

The non-elastic, non-stretchable continuous crotch web 118 which is shown in the figures, is a crotch panel web, being applied only to bridge the gap 115 between the front panel web 101 and the rear panel web 108. As set out herein, the non-elastic continuous crotch web may alternatively be an outer or inner cover web extending in the cross machine direction the full distance or at least 75% of the distance between the front waist edge and the rear waist edge.

Figure 3:
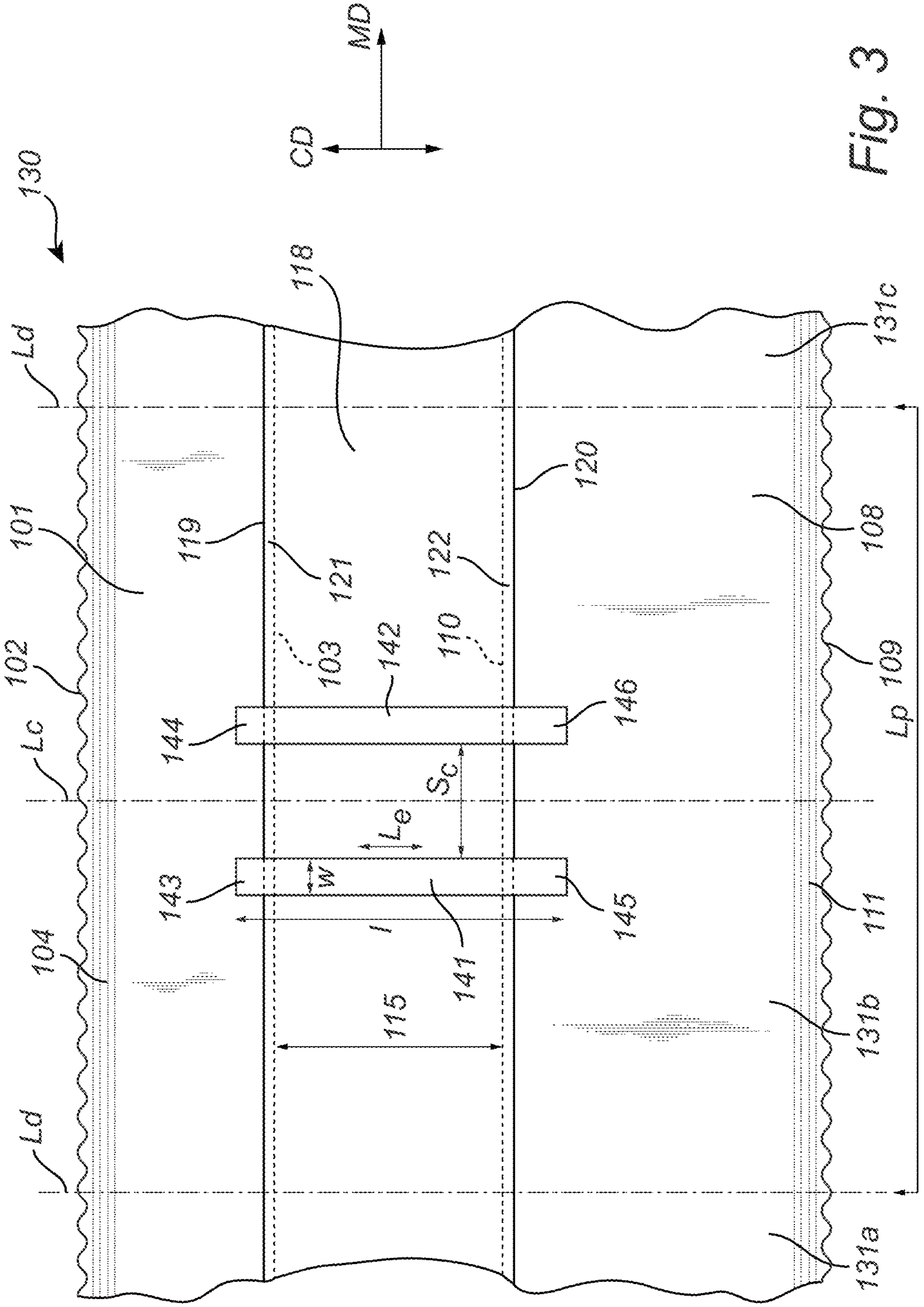

With reference to FIG. 3, a pair of crotch elastic members is provided consisting of a first band-shaped crotch elastic member 141 and a second band-shaped crotch elastic member 142.

Each crotch elastic member 141, 142 is stretched in a longitudinal direction Le of the crotch elastic member and the longitudinal direction $L_e$ of the crotch elastic member 141,142 is aligned with the cross machine direction CD of the moving chassis web 130.

Each stretched crotch elastic member 141, 142 is then attached to the chassis web 130 while keeping the crotch elastic member 141, 142 stretched and aligned with the cross machine direction CD. The pair of crotch elastic members is attached to the chassis web 130 with the first crotch elastic member 141 being spaced apart from the second crotch elastic member 142 with a crotch spacing $S_c$ in the machine direction and are symmetrically placed on each side of a precursor article centerline Lc extending in the cross machine direction CD. The pairs of crotch elastic members of the precursor articles 131*a*, 131*b*, 131*c* are spaced apart in the machine direction with an article spacing corresponding to the pitch-length of the precursor articles 131*a*, 131*b*, 131*c*. In the moving chassis web 130 which is shown in the Figures, a first end portion 143,144 of each of the first and the second crotch elastic members 141,142 is overlapped with and attached to the tensioned front panel web 101 and a second end portion 145,146 of each of the first and the second crotch elastic members 141, 142 is overlapped with and attached to the tensioned rear panel web 108.

When stretching and applying the stretched crotch elastic members 141, 142 to the chassis web, the first and second end portions 143, 144, 145, 146 of the crotch elastic members 141, 142 may be held in movable clamps in a stretching device (not shown). The clamped end portions 143, 144, 145, 146 are not subjected to stretching and are applied and attached to the chassis web 130 in a non-tensioned condition.

The stretched crotch elastic members 141, 142 may have a width w as measured in the machine direction MD in the range of from 15 mm to 50 mm and a length l as measured in the cross machine direction in the range of from 150 mm to 350 mm.

In a preferred embodiment of the method as disclosed herein the elastic members comprise or consist of elastic film.

Figure 4:
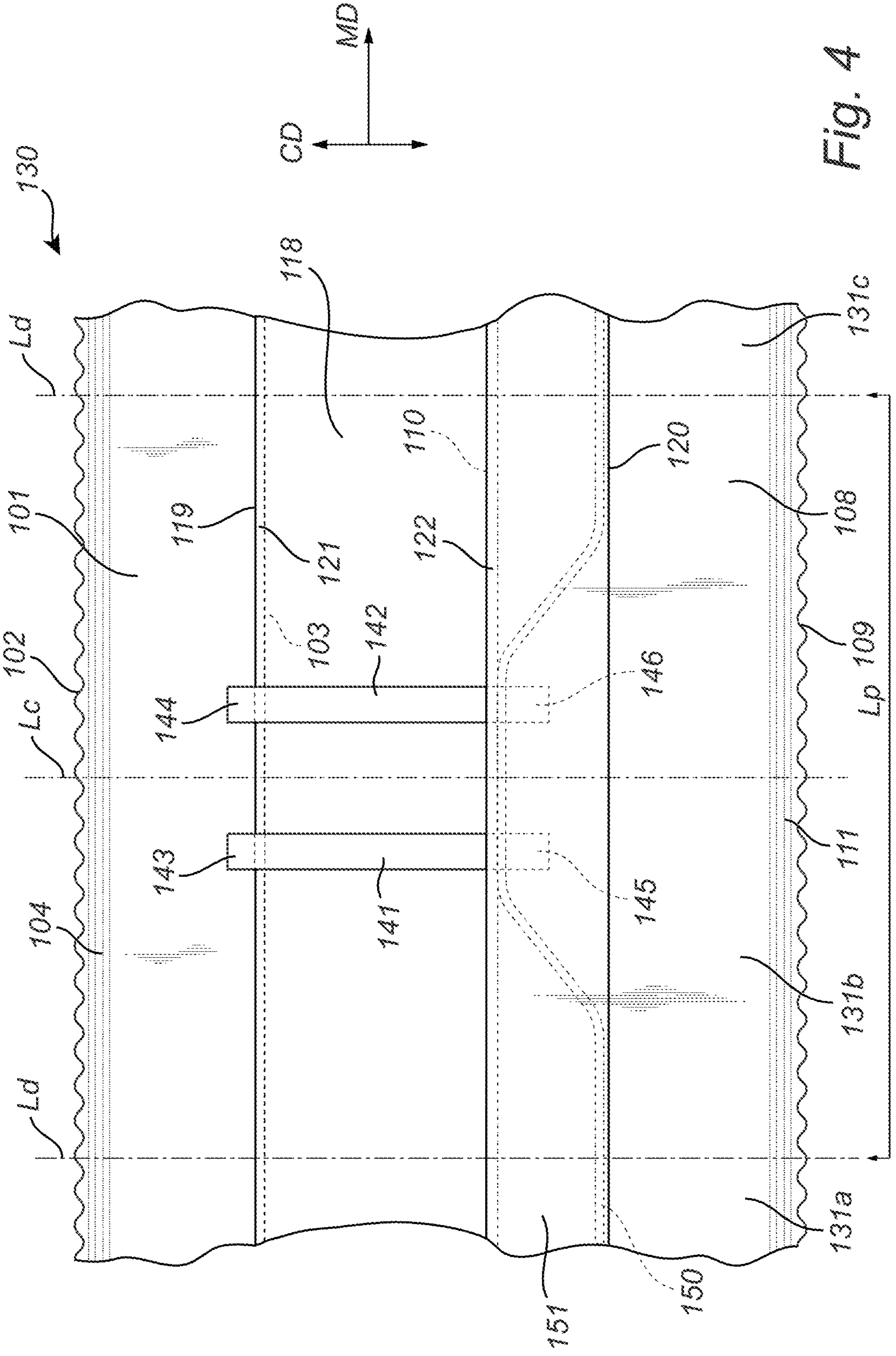

With reference to FIG. 4, a continuous reinforcing leg elastic member 150 is stretched in the machine direction MD and is attached in a stretched state in a curved configuration along the crotch edge 110 of the tensioned rear panel web 108.

The reinforcing leg elastic member 150 is attached in an attachment area or multiple attachment areas (not shown) created on the tensioned rear panel web 108 by continuously or discontinuously applying adhesive to selected portions of the tensioned rear panel web 108 prior to application of the reinforcing leg elastic member 150. After attachment of the reinforcing leg elastic member 150 the leg elastic member 150 and any exposed adhesive may be covered with a nonwoven covering web 151, as shown in FIG. 4.

The reinforcing leg elastic member 150 intersect with and are attached to the preferably non-tensioned second end portions 145, 146 of the first and second crotch elastic members 141, 142.

Figure 5:
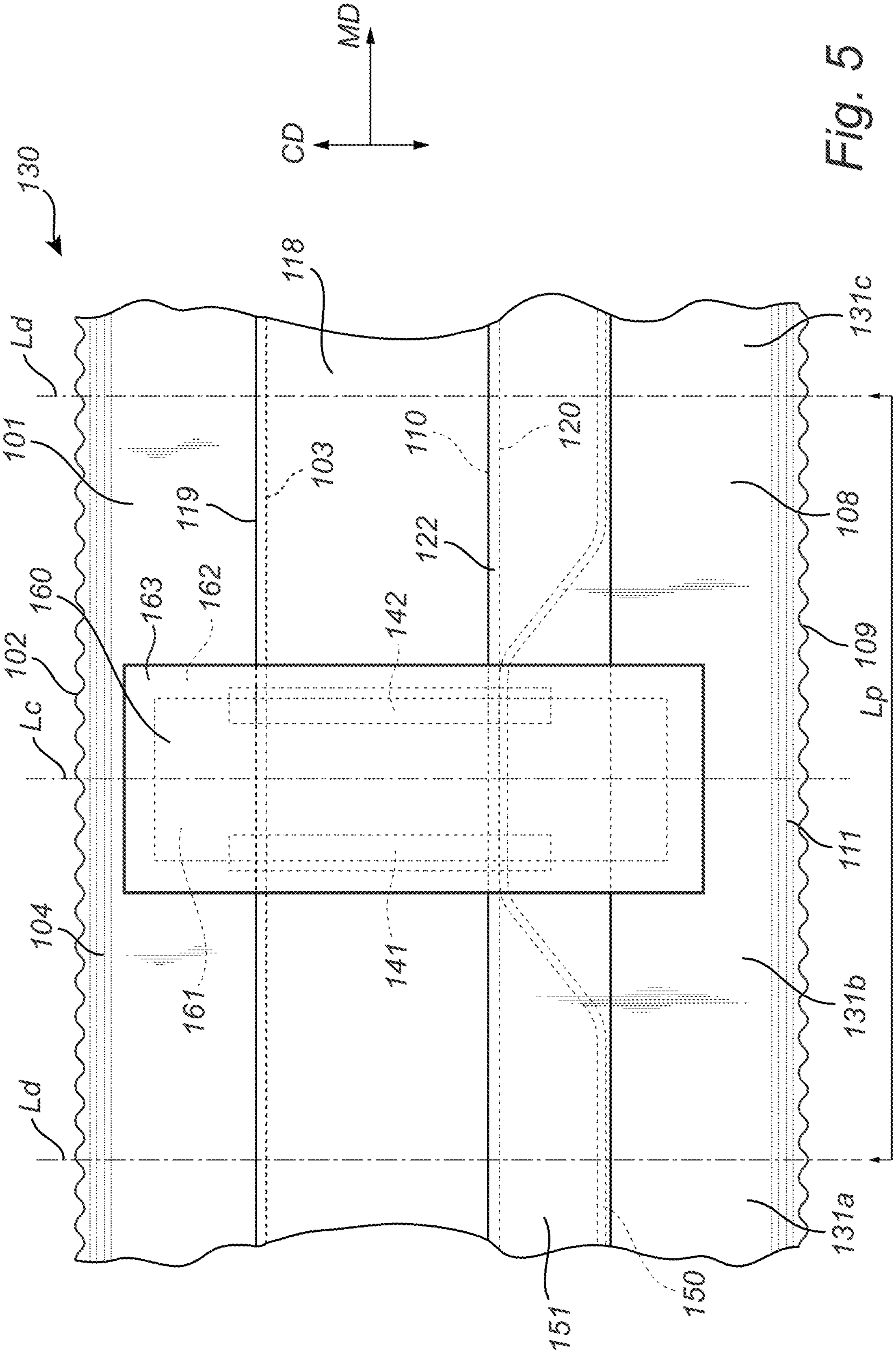

As illustrated in FIG. 5, the method may further comprise applying and attaching an absorbent assembly 160 comprising an absorbent core 161 to the moving chassis web 130. The absorbent assembly 161 further comprises a liquid impermeable backsheet 162 and a liquid permeable topsheet 163 which together enclose the absorbent core 161.

The absorbent assembly 160 is applied on the precursor article centerline Lc and covers the stretched and attached crotch elastic members 141, 142.

The absorbent core 161 is disposed between the topsheet 163 and the backsheet 162 to absorb liquid, such as urine or other bodily fluids, which has passed through the topsheet 163.

The topsheet 163, backsheet 162 and the absorbent core 161 may consist of any materials suitable for their purposes.

The absorbent core 161 may be a single-layer structure or may be a layered structure. The absorbent core 161 may comprise suitable amounts of superabsorbent material. Such superabsorbent material is well known in the field of absorbent articles and is constituted by water-swellable and water-insoluble material which is capable of absorbing large quantities of fluid upon formation of a hydrogel. The absorbent core 161 may contain superabsorbent material in the form of fibers or particles of absorbent polymer material.

For example, the superabsorbent material may be surface cross-linked, partially neutralized polyacrylates. The superabsorbent material e.g., the superabsorbent fibers or particles, may be mixed with other absorbent or liquid uptake material or materials, such as cellulose fluff pulp, and/or be arranged in pockets or layers in the absorbent core 161.

The absorbent core 161 may further comprise components for improving properties of the absorbent core 161, such as integrity and strength. For example, the absorbent core 161 may comprise a binder or binders, such as binder fibers. Resilient fibers, chemically stiffened fibers, etc. may be present in the absorbent core 161 to counteract wet-collapse of cellulosic fibers. Such fibers may also be useful in retaining a fluid transporting capillary network in the absorbent component so that absorbent fluid may be distributed in the absorbent component and be absorbed by superabsorbent material also in parts of the absorbent component outside the initial wetting area of the absorbent article.

The topsheet 163 is a wearer-facing layer and may comprise or consist of a fluid permeable nonwoven fabric, a perforated polymer film, mesh or foam. The topsheet may be made from thermoplastic material, such as thermoplastic synthetic fibers, film or netting. The topsheet 163 may consist of a single layer or may have a laminate structure comprising a plurality of layers, for example, two or more layers. The layers may be made of the same material, or some or all layers may be made of different materials.

Furthermore, the backsheet 162 may be constituted by a liquid-impermeable layer such as a polymeric film, for example a film of polyethylene or polypropylene. The backsheet 162 may be breathable. The materials which may be used for the backsheet 162 include thin and flexible fluid impermeable plastic films, or fluid impermeable nonwoven materials, fluid impermeable foams and fluid impermeable laminates. The backsheet 162 may be formed by a single layer, or may be a multi-layered structure, with at least one layer being fluid impermeable.

Figure 6:
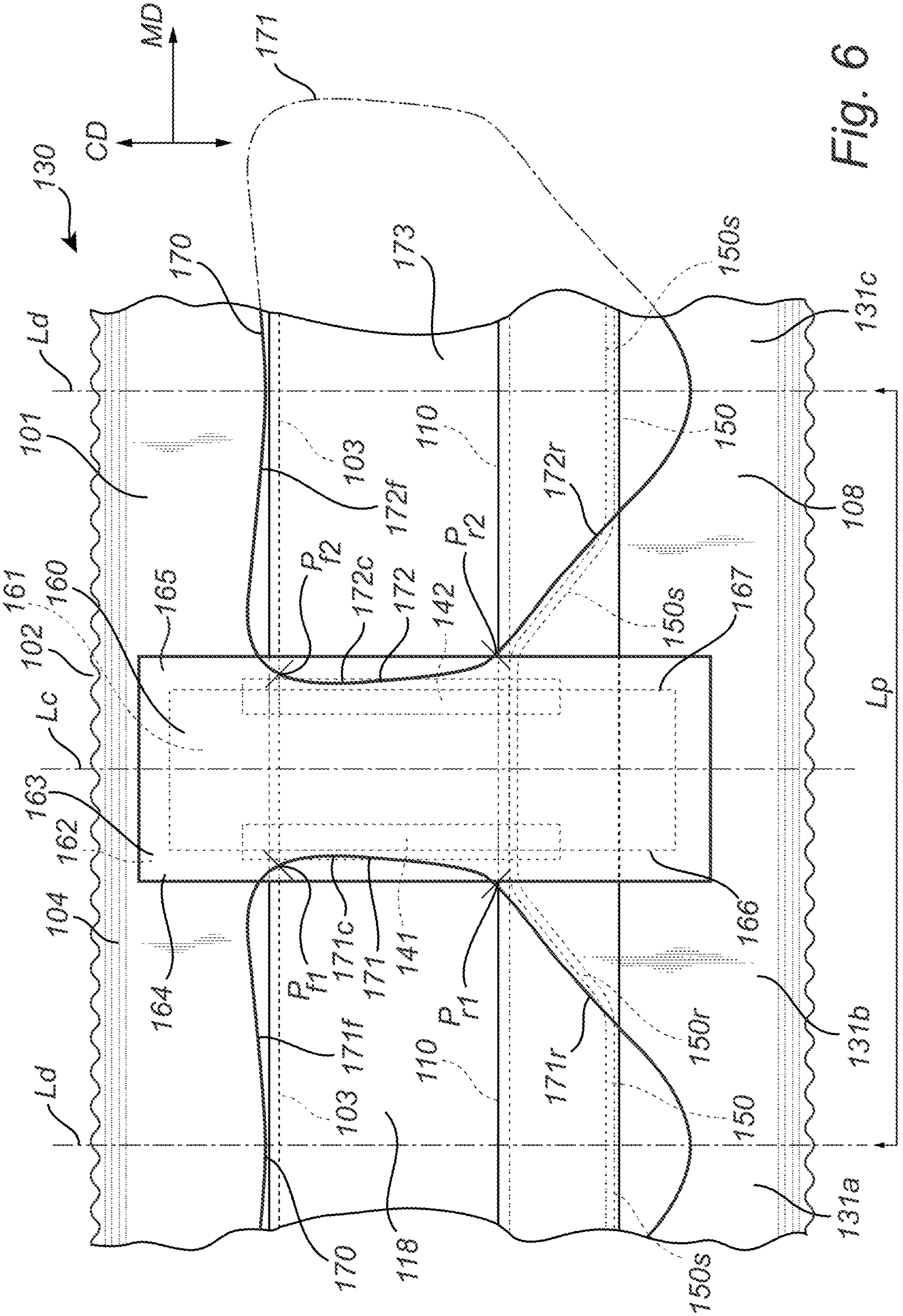

After the optional application and attachment of an absorbent assembly 160 to the chassis web 130, leg cuts 170 are formed in the chassis web 130 between the precursor articles 131*a*, 131*b*, 131*c*, each leg cut 170 having a closed loop configuration as indicated between the precursor articles 131*b* and 131*c* in FIG. 6. The leg cuts form a first leg edge 171 of the leading precursor article 131*c* and a second leg edge of the trailing precursor article 131*b*.

As shown in FIG. 6, the first leg edge 171 of each precursor article 131*a*, 131*b*, 131*c* in the chassis web 130 consists of:

- a front leg edge section 171*f* extending in the tensioned front panel web 101;
- a crotch leg edge section 171*c* extending in the crotch web 118 between the front panel crotch edge 103 and the rear panel crotch edge 110; and
- a rear leg edge section 171*r* extending in the tensioned rear panel web 108.

The second leg edge 172 of each precursor article 131*a*, 131*b*, 131*c*, consists of:

- a front leg edge section 172*f* extending in the tensioned front panel web 101;
- a crotch leg edge section 172*c* extending in the crotch web 118 between the front panel crotch edge 103 and the rear panel crotch edge 110; and
- a rear leg edge section 172*r* extending in the tensioned rear panel web 108.

The reinforcing leg elastic member 150 is not attached to the chassis web 130 in the area which is located between the leg edges 171, 172 where the absorbent core 161 is located, The reinforcing leg elastic member 150 is rendered inactive in the area between the leg edges 171, 172 by being severed at the precursor article centerline Lc and allowed to snap-back to attachment areas arranged at the intersections between the rear leg edge sections and the crotch leg edge sections.

As shown in FIG. 6, the closed-loop leg cuts 170 form cut-out portions 173 inside each leg cut 170. In FIG. 6, the material in the cut-out portions 173 remain inside the leg cuts 170 while in FIG. 7 the material in the cut-out portions 173 has been removed from the chassis web 130. In the example shown in FIG. 6, the cut-out portions 173 have an approximate heart-shape. However, it is to be understood that the shape of the cut-out portions 173 may be varied e.g., to adapt the fit of the pant-type article as disclosed herein to the body size and shape of a particular category of users. After forming the leg cuts 170, the cut-out portions 173 are removed from the chassis web and are not further part of the process as disclosed herein.

The length of each of the crotch leg edge sections 171*c*, 172*c*, is measured along the corresponding leg edge 171, 172 from a forward point Pf1, Pf2 on the leg edge 171, 172 where the leg edge 171, 172 intersects with the front panel crotch edge 103 to a rearward point Pr1, Pr2 on the leg edge 171, 172 where the leg edge 171, 172 intersects with the rear panel crotch edge 110.

The length of the front leg edge section 171*f* of the first leg edge 171 is measured along the first leg edge 171 from the forward point Pf1 on the first leg edge 171 where the first leg edge 171 intersects with the front panel crotch edge 103, to the dividing line Ld which is behind the first leg edge 171 in the machine direction MD that is, to the dividing line Ld which is closest to the forward point Pf1.

The length of the rear leg edge section 171*r* of the first leg edge 171 is measured along the first leg edge 171 from the rearward point Pr1 on the first leg edge 171 where the first leg edge 171 intersects with the rear panel crotch edge 108, to the dividing line Ld which is behind the first leg edge 171 in the machine direction MD that is, to the dividing line Ld which is closest to the rearward point Pr1.

The length of the front leg edge section 172*f* of the second leg edge 172 is measured along the second leg edge 172 from the forward point Pf2 on the second leg edge where the second leg edge 172 intersects with the front panel crotch edge 103, to the dividing line Ld which is in front of the second leg edge 172, in the machine direction MD that is, to the dividing line Ld which is closest to the forward point Pf2.

The length of the rear leg edge section 172*r* of the second leg edge 172 is measured along the second leg edge 172 from the rearward point Pr2 on the second leg edge 172 where the second leg edge 172 intersects with the rear panel crotch edge 108 to the dividing line Ld which is in front of the second leg edge 172 in the machine direction MD that is, to the dividing line Ld which is closest to the rearward point Pr2.

After forming the leg cuts, the absorbent assemblies 160 will be located centrally between the first leg edge 171 and the second leg edge of each precursor article 131*a*, 131*b*, 131*c* in the chassis web.

As shown in FIG. 6, a part of each crotch leg edge section 171*c*, 172*c* may be formed by cutting through the crotch web 118, through the corresponding crotch elastic member 141, 142 and through a peripheral edge portion 164, 165 of the absorbent assembly 160. The peripheral edge portions 164, 165 of the absorbent assembly 160 are formed by portions of the liquid impermeable backsheet 162 and the liquid permeable topsheet 163 of the absorbent assembly 160 which extend in the machine direction MD outward of a corresponding peripheral edge 166, 167 of the absorbent core 161 of the absorbent assembly 160. In the absorbent assembly 160 shown in the Figures, the topsheet 163 and the backsheet 162 both extend beyond the peripheral edges 166, 167 of the absorbent core 161 and are joined to each other in an edge seal.

The crotch leg edge sections 171*c*, 172*c* are cut with a slightly concave curvature, as seen in FIG. 6 such that also the band-shaped crotch elastic members 141, 142 which initially have a generally rectangular shape are given a somewhat modified band-shape with a concave cut edge along at least part of the crotch leg edge sections 171*c*, 172*c*.

Figure 7:
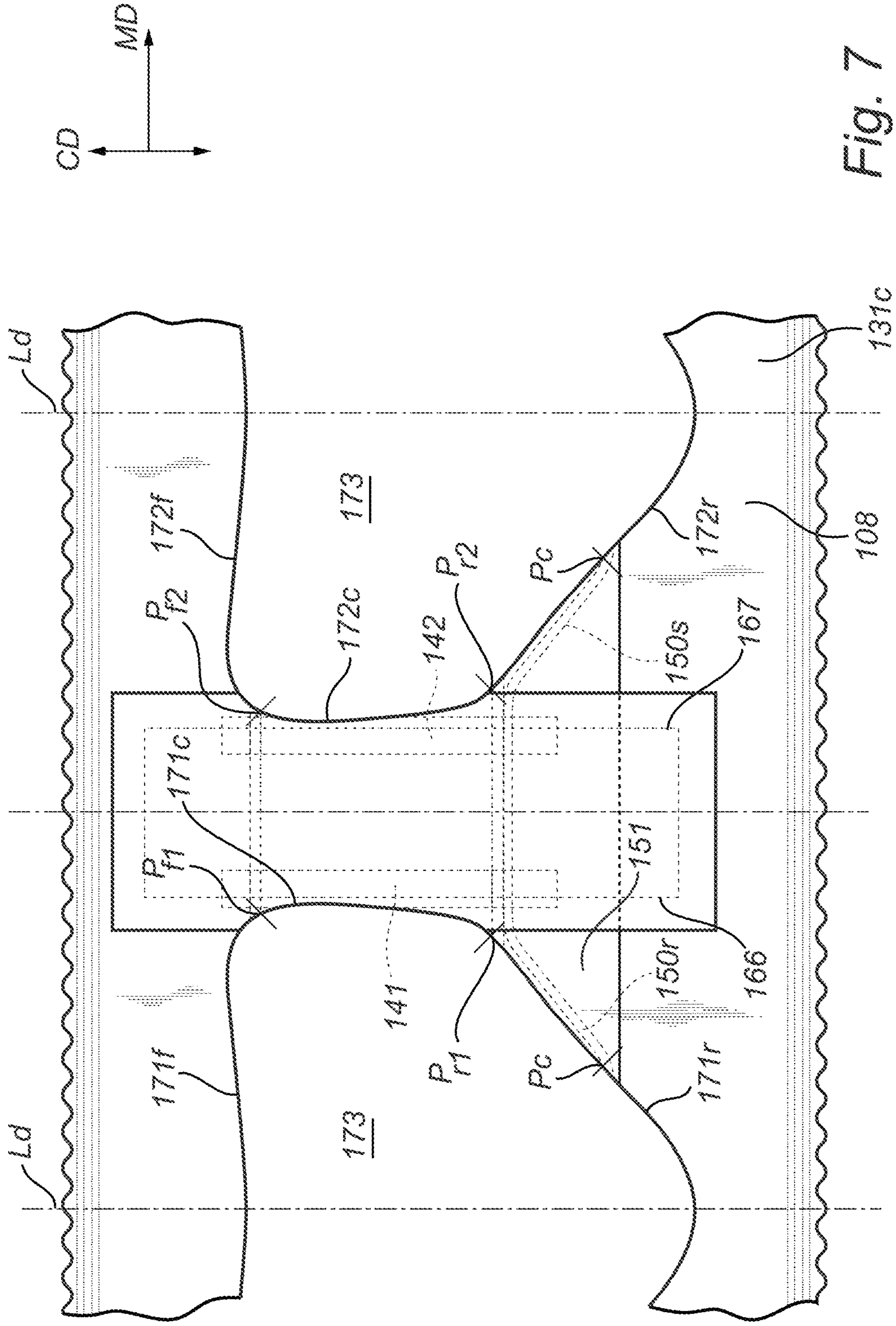

With further reference to FIG. 6 and to FIG. 7, when cutting the rear leg edge sections 171*r*, 172*r* of the first and second leg edges 171, 172 surplus parts 150*s* of the reinforcing elastic element 150 are simultaneously cut away together with the cut-out portion 173, leaving a remaining part 150*r* of the reinforcing elastic element 150 being attached along the rear leg edge section 171*r*, 172*r* of each of the first leg edge 171 and the second leg edge 172 between the rearward point Pr1, Pr2 of each leg edge 171, 172 where the leg edge 171, 172 intersects with the rear panel crotch edge 110 and the cutting point Pc on the leg edge where the reinforcing elastic element 150 is cut off. Thereby, a portion of each rear leg edge section 171*r*, 172*r* between the cutting point Pc and the dividing line Ld which is closest to the cutting point Pc, is free from reinforcing elastic. The portion of each rear leg edge section 171*r*, 172*r* which is free from the reinforcing elastic element 150 may have a length as measured along the corresponding leg edge 171, 172 from the cutting point Pc to the closest dividing line Ld which is from 25% to 75% of the total length of the rear leg edge section 171*r*, 172*r*.

Figure 8:
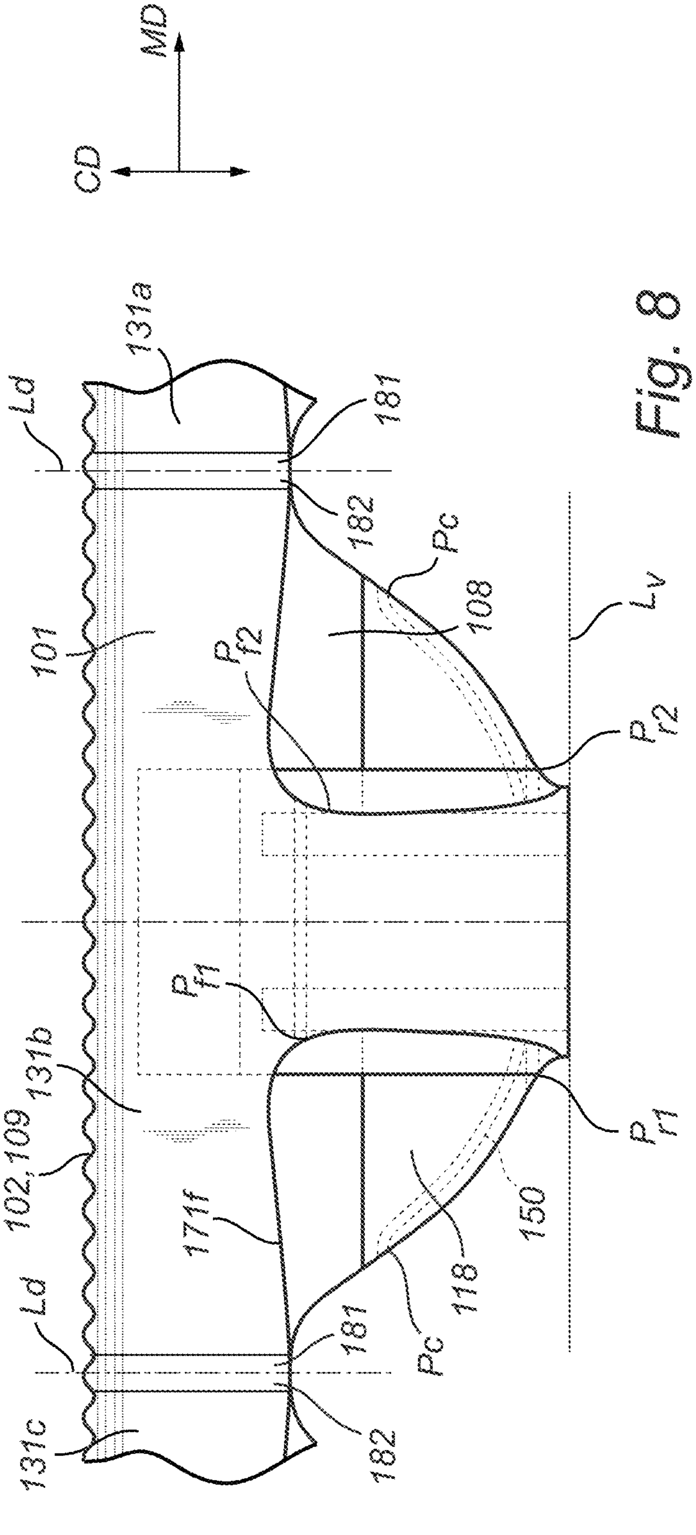
FIG. 8 shows a planar view of a section of the chassis web in FIGS. 1-7 in a final stages of production.

After forming the leg edges 171, 172 by cutting out the cut-out portion 173 from the chassis web 130 along the cutting line 170, the chassis web 130 is folded along a fold-line Lv extending in the machine direction MD to bring the waist edge 102 of the front panel web 101 into alignment with the waist edge 109 of the rear panel web 108 as shown in FIG. 8.

A first side seam 181 and a second side seam 182 are formed in each precursor article 131*a*, 131*b*, 131*c* along the dividing lines Ld between the precursor articles 131*a*, 131*b*, 131*c*, from the aligned waist edges 102, 109 of the front and rear panel webs 101, 108, to the leg cuts 170.

The first side seam 181 of a leading precursor article 131*a* and the second side seam 182 of a trailing precursor article 131*b* may be formed as a single broad seal extending along the dividing line Ld, as shown in FIG. 8. When cutting away individual pant-type articles from the chassis web 130 of precursor articles 131*a*, 131*b*, 131*c* by severing the chassis web along the dividing lines Ld, the single broad seal shown in FIG. 8 will at the same time be divided into the two side seams 181, 182 of the interconnected precursor articles 131*a*, 131*b*.

Alternatively, the side seams 181, 182 may be formed as individual seals placed on each side of the dividing line Ld.

The side seams may be formed by any method suitable for the purpose, such as by thermo-welding, ultrasonic welding or by means of adhesive. In case of adhesive side seals, the adhesive is generally applied before the chassis web is folded along the folding line Lv.

Figure 9:
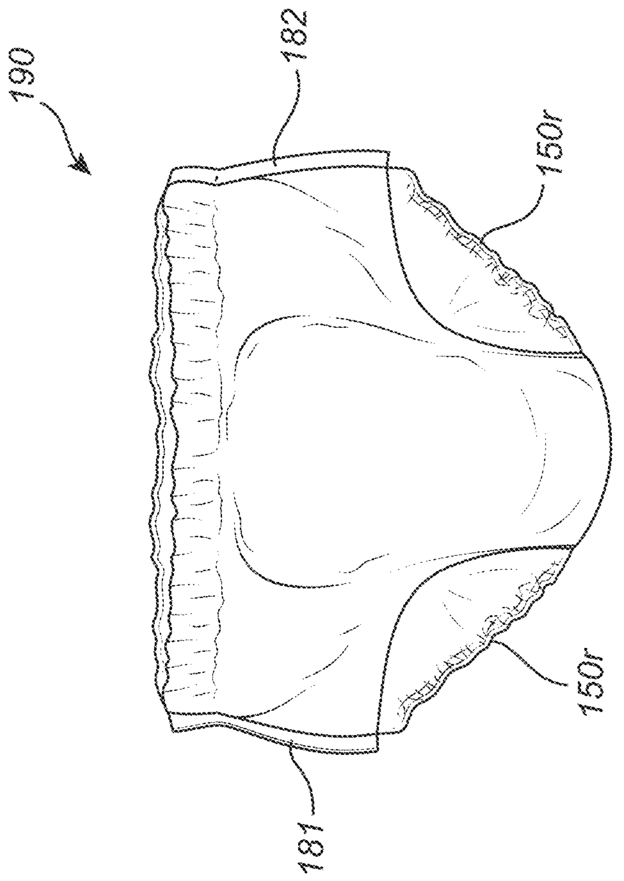
FIG. 9 shows a pant type absorbent article.

FIG. 9 shows a disposable pant-type article 190 after it has been cut away from the chassis web 130 of precursor articles 131*a*, 131*b*, 131*c*. The disposable pant-type article 190 is shown with all elastic elements which have been stretched out during production retracted to a relaxed state, causing the web materials in the pant-type article 190 to gather.

The invention claimed is:

1. A method of producing disposable pant-type articles, the method comprising the steps of:

advancing a continuous elastic front panel web in a machine direction, the front panel web being tensioned in the machine direction and having a front panel waist edge and an opposing front panel crotch edge;

advancing a continuous elastic rear panel web in a machine direction, the rear panel web being tensioned in the machine direction and having a rear panel waist edge and an opposing rear panel crotch edge, the rear panel web being spaced apart from the front panel web in a cross machine direction, perpendicular to the machine direction, with a gap in the cross machine direction between the front panel crotch edge and the rear panel crotch edge;

advancing a non-elastic continuous crotch web in the machine direction;

attaching the crotch web to the tensioned front panel web and to the tensioned rear panel web, thereby bridging the gap between the front panel crotch edge and the rear panel crotch edge and forming a coherent chassis web of interconnected precursor articles;

providing a pair of crotch elastic members, the pair of crotch elastic members consisting of a first crotch elastic member and a second crotch elastic member;

stretching each crotch elastic member in a longitudinal direction of the crotch elastic member and aligning the longitudinal direction of the crotch elastic member with the cross machine direction;

attaching each stretched crotch elastic member to the crotch web while keeping the crotch elastic member stretched and aligned with the cross machine direction, the first crotch elastic member being spaced apart from the second crotch elastic member with a crotch spacing in the machine direction, a pair of crotch elastic members of a leading precursor article being spaced apart from a pair of crotch elastic members of a trailing precursor article with an article spacing in the machine direction, the article spacing being dependent on a pitch-length of the precursor articles in the chassis web of interconnected precursor articles;

forming leg cuts in the chassis web, each leg cut having a closed loop configuration and forming a first leg edge of a leading precursor article and a second leg edge of a trailing precursor article;

folding the chassis web along a fold-line extending in the machine direction and bringing the front panel waist edge into alignment with the rear panel waist edge;

forming first and second side seams in each precursor article, the side seams being formed in the cross machine direction along dividing lines between the precursor articles, from the aligned waist edges of the front and rear panel webs, to the leg cuts; and severing individual pant-type articles from the chassis web, wherein the method further comprises applying and attaching an absorbent assembly comprising an absorbent core to each precursor article in the chassis web, the absorbent core of the absorbent assembly being enclosed between a liquid impermeable backsheet and a liquid permeable topsheet, and wherein the absorbent assembly is applied to completely cover the stretched and attached crotch elastic members.

2. A method according to claim 1, wherein the non-elastic continuous crotch web is a crotch panel web having a first side edge and an opposing second side edge, and wherein attaching the crotch web to the tensioned front panel web and to the tensioned rear panel web comprises;

attaching the first side edge of the crotch web to the tensioned front panel web along the front panel crotch edge, such as in an overlap seam extending along the front panel crotch edge; and attaching the second side edge of the crotch web to the tensioned rear panel web along the rear panel crotch edge; such as in an overlap seam extending along the rear panel crotch edge.

3. A method according to claim 1, wherein the elastic front panel web is constituted by an elastic laminate web comprising an elastic film and/or an elastic nonwoven web or is constituted by an elastic nonwoven web, and the elastic rear panel web is constituted by an elastic laminate web comprising an elastic film and/or an elastic nonwoven web or is constituted by an elastic nonwoven web.

4. A method according to claim 1, wherein the crotch elastic members are band-shaped crotch elastic members.

5. A method according to claim 4, wherein the stretched crotch elastic members have a width as measured in the machine direction in the range of from 15 mm to 50 mm and a length as measured in the cross machine direction in the range of from 150 mm to 350 mm.

6. A method according to claim 1, wherein the crotch elastic members comprise or consist of elastic film.

7. A method according to claim 1, wherein the crotch elastic members comprise or consist of elastic nonwoven.

8. A method according to claim 1, wherein a part of each leg cut which extends in the crotch web is cut through the crotch web, the corresponding crotch elastic member and a peripheral edge portion of one or both of the liquid impermeable backsheet and the liquid permeable topsheet, the peripheral edge portion being arranged outward of a periphery of the absorbent core of the absorbent assembly.

9. A method according to claim 1, wherein a continuous reinforcing leg elastic member is stretched in the machine direction and is attached in a stretched state in a curved configuration along the rear panel crotch edge before forming the leg cuts in the chassis web.

10. A method according to claim 9, wherein attaching the continuous reinforcing elastic element comprises forming an attachment area or multiple attachment areas on the tensioned rear panel web by applying adhesive to the tensioned rear panel web;

attaching the continuous reinforcing elastic element to the tensioned rear panel web in the attachment area or attachment areas; and optionally covering the reinforcing elastic element and the attachment area or attachment areas with a nonwoven covering web.

11. A method according to claim 1, wherein the first leg edge of each precursor article in the chassis web consists of:

a front leg edge section extending in the tensioned front panel web;

a crotch leg edge section extending in the crotch web between the front panel crotch edge and the rear panel crotch edge; and a rear leg edge section extending in the tensioned rear panel web; and the second leg edge of each precursor article consists of:

a front leg edge section extending in the tensioned front panel web;

a crotch leg edge section extending in the crotch web between the front panel crotch edge and the rear panel crotch edge; and a rear leg edge section extending in the tensioned rear panel web.

12. A method according to claim 11, wherein the method comprises forming the rear leg edge section of the first and second leg edges and simultaneously cutting away surplus parts of the reinforcing elastic element, leaving a remaining part of the reinforcing elastic element being attached along the rear leg edge section of each of the first leg edge and the second leg edge; each rear leg edge section being free from the reinforcing elastic element in a portion of the rear leg edge section located between a cutting point on the leg edge where the reinforcing elastic element is cut off, and a dividing line between adjacent precursor articles which is located closest to the cutting point, the portion of each rear leg edge section which is free from the reinforcing elastic element having a length as measured along the corresponding leg edge from the cutting point to the closest dividing line which is from 25% to 75% of the total length of the rear leg edge section.

13. A method according to claim 1, wherein the method comprises attaching a waist elastic member along the front panel waist edge and/or along the rear panel waist edge, the waist elastic member or waist elastic members being attached before or after attaching the crotch web to the front panel web and the rear panel web.

14. A method of producing disposable pant-type articles, the method comprising the steps of:

advancing a continuous elastic front panel web in a machine direction, the front panel web being tensioned in the machine direction and having a front panel waist edge and an opposing front panel crotch edge;

advancing a continuous elastic rear panel web in a machine direction, the rear panel web being tensioned in the machine direction and having a rear panel waist edge and an opposing rear panel crotch edge, the rear panel web being spaced apart from the front panel web in a cross machine direction, perpendicular to the machine direction, with a gap in the cross machine direction between the front panel crotch edge and the rear panel crotch edge;

advancing a non-elastic continuous crotch web in the machine direction;

attaching the crotch web to the tensioned front panel web and to the tensioned rear panel web, thereby bridging the gap between the front panel crotch edge and the rear panel crotch edge and forming a coherent chassis web of interconnected precursor articles;

providing a pair of crotch elastic members, the pair of crotch elastic members consisting of a first crotch elastic member and a second crotch elastic member;

stretching each crotch elastic member in a longitudinal direction of the crotch elastic member and aligning the longitudinal direction of the crotch elastic member with the cross machine direction;

attaching each stretched crotch elastic member to the crotch web while keeping the crotch elastic member stretched and aligned with the cross machine direction, the first crotch elastic member being spaced apart from the second crotch elastic member with a crotch spacing in the machine direction, a pair of crotch elastic members of a leading precursor article being spaced apart from a pair of crotch elastic members of a trailing precursor article with an article spacing in the machine direction, the article spacing being dependent on a pitch-length of the precursor articles in the chassis web of interconnected precursor articles;

forming leg cuts in the chassis web, each leg cut having a closed loop configuration and forming a first leg edge of a leading precursor article and a second leg edge of a trailing precursor article;

folding the chassis web along a fold-line extending in the machine direction and bringing the front panel waist edge into alignment with the rear panel waist edge;

forming first and second side seams in each precursor article, the side seams being formed in the cross machine direction along dividing lines between the precursor articles, from the aligned waist edges of the front and rear panel webs, to the leg cuts; and severing individual pant-type articles from the chassis web, wherein a continuous reinforcing leg elastic member is stretched in the machine direction and is attached in a stretched state in a curved configuration along the rear panel crotch edge before forming the leg cuts in the chassis web, wherein the method comprises overlapping a first end portion of each of the first and the second crotch elastic members of the pair of crotch elastic members with the tensioned front panel web and attaching the overlapping first end portion of each of the first and the second crotch elastic member to the tensioned front panel web and/or overlapping a second end portion of each of the first and the second crotch elastic members of the pair of crotch elastic members with the tensioned rear panel web and attaching the overlapping second end portion of each of the first and the second crotch elastic member to the tensioned rear panel web.

15. A method according to claim 14, wherein the second end portion of each of the first and the second crotch elastic members overlaps with and is attached to the tensioned rear panel web, and further is attached to the reinforcing elastic element.

16. A method according to claim 15, wherein the first and second crotch elastic members are attached to the chassis web before or after attaching the reinforcing elastic element.

17. A disposable pant-type article being produced by the method in claim 1.

* * * * *